(12) United States Patent
Couchou-Meillot

(10) Patent No.: US 11,486,808 B2
(45) Date of Patent: Nov. 1, 2022

(54) DETERMINATION OF PROPERTIES OF A HYDROCARBON FLUID

(71) Applicant: Total S.A., Courbevoie (FR)

(72) Inventor: Gilles Couchou-Meillot, Pau (FR)

(73) Assignee: TOTAL SE, Courbevoie (FR)

( * ) Notice: Subject to any disclaimer, the term of this patent is extended or adjusted under 35 U.S.C. 154(b) by 186 days.

(21) Appl. No.: 16/644,385

(22) PCT Filed: Sep. 5, 2017

(86) PCT No.: PCT/IB2017/001188
§ 371 (c)(1),
(2) Date: Mar. 4, 2020

(87) PCT Pub. No.: WO2019/048899
PCT Pub. Date: Mar. 14, 2019

(65) Prior Publication Data
US 2021/0063293 A1 Mar. 4, 2021

(51) Int. Cl.
*G01N 7/00* (2006.01)
*G01N 25/16* (2006.01)
(Continued)

(52) U.S. Cl.
CPC .......... *G01N 7/00* (2013.01); *E21B 49/0875* (2020.05); *G01N 1/18* (2013.01); *G01N 25/16* (2013.01); *G01N 33/2841* (2013.01)

(58) Field of Classification Search
CPC ...... G01N 7/00; G01N 25/16; G01N 33/2841; E21B 49/087; E21B 49/0875
See application file for complete search history.

(56) References Cited

U.S. PATENT DOCUMENTS 3,528,439 A * 9/1970 Plucker .................... G01N 7/00
137/3
3,780,590 A 12/1973 Stamm
(Continued)

FOREIGN PATENT DOCUMENTS

FR 3 033 893 9/2016
WO WO 96/10745 4/1996
(Continued)

OTHER PUBLICATIONS

International Search Report for International App. No. PCT/IB2017/001188, dated May 8, 2018, in 3 pages.
(Continued)

*Primary Examiner* — Paul M. West
(74) *Attorney, Agent, or Firm* — Knobbe Martens Olson & Bear, LLP

(57) ABSTRACT

The invention relates to a method for determining at least one property of hydrocarbon fluid, comprising: (a) providing a first chamber (1) filled with the hydrocarbon fluid and a second chamber (2) which is substantially empty, each of the first chamber (1) and second chamber (2) having a fixed volume; (b) transferring a sample of hydrocarbon fluid from the first chamber (1) to the second chamber (2); (c) measuring a pressure in at least one of the first chamber (1) and the second chamber (2); (d) repeating steps (b) and (c) a plurality of times. The invention also relates to an apparatus for implementing this method.

20 Claims, 4 Drawing Sheets

(51) Int. Cl.
*G01N 33/28* (2006.01)
*E21B 49/08* (2006.01)
*G01N 1/18* (2006.01)

(56) References Cited

U.S. PATENT DOCUMENTS

| | | | |
|---|---|---|---|
| 4,543,819 A * | 10/1985 | Chin | G01N 7/14 137/88 |
| 2002/0059907 A1 | 5/2002 | Thomas | |
| 2007/0119244 A1 * | 5/2007 | Goodwin | G01N 33/2823 73/152.28 |
| 2016/0168933 A1 | 6/2016 | Aktas et al. | |

FOREIGN PATENT DOCUMENTS

| WO | WO 2011/014202 | 2/2011 |
|---|---|---|
| WO | WO 2016/094474 | 6/2016 |

OTHER PUBLICATIONS

European Office Action in EP 17 784 995.7 dated Aug. 10, 2022 in 7 pages.

* cited by examiner

DETERMINATION OF PROPERTIES OF A HYDROCARBON FLUID

TECHNICAL FIELD

The present invention relates to a method for determining at least one property of a hydrocarbon fluid, such as e.g. compressibility, vapor pressure, gas/oil volume ratio, etc. as well an apparatus suitable for implementing this method.

TECHNICAL BACKGROUND

Hydrocarbon fluids contained in or recovered from subterranean formations are complex fluids containing many different chemical compounds.

In order to optimize hydrocarbon recovery in a process of extracting hydrocarbons from a subterranean formation, it is necessary to know the physical properties of the hydrocarbon fluid, in order to anticipate its volumetric and phase behavior as it travels from the subterranean formation up to surface capabilities, including separators and pipelines for instance, as well as the volumetric and phase behavior of the portion of the fluid remaining in the subterranean formation.

These physical properties, such as viscosity, density, compressibility, depend on pressure and temperature.

Conventionally, these properties are determined owing to a so-called pressure-volume-temperature (PVT) analysis. The PVT analysis is usually performed as follows:
- a chamber having an adjustable volume, for instance owing to a piston, is provided;
- a sample of hydrocarbon fluid is introduced into the chamber under relatively high pressure, and the chamber is sealed;
- the volume of the chamber is increased, e.g. by moving the piston; and
- the pressure in the chamber is measured.

From this measurement, various properties of the hydrocarbon fluid may be determined.

This conventional method raises a number of practical issues. In particular, due to the high pressure which is applied, it is necessary to use a large piston. This, in turn, implies that the chamber must have a large volume. The equipment used for the PVT analysis is thus very bulky and inconvenient to use on an extraction field. At the very least, it is impossible to introduce said equipment into an extraction well.

Ensuring tightness of the equipment is also a challenge.

Furthermore, due to the large volume of the chamber, the equipment has a large dead volume, which may result in poor accuracy.

There is thus a need for an improved method of measuring properties of a complex hydrocarbon fluid, which is easier to implement and relies on equipment having a smaller size.

SUMMARY OF THE INVENTION

It is a first object of the invention to provide a method for determining at least one property of a hydrocarbon fluid, comprising:
- (a) providing a first chamber filled with the hydrocarbon fluid and a second chamber which is substantially empty, each of the first chamber and second chamber having a fixed volume;
- (b) transferring a sample of hydrocarbon fluid from the first chamber to the second chamber;
- (c) measuring a pressure in at least one of the first chamber and the second chamber;
- (d) repeating steps (b) and (c) a plurality of times.

In some embodiments, step (c) comprises measuring a pressure both in the first chamber and in the second chamber.

In some embodiments, all successive samples of step (b) have a fixed volume.

In some embodiments, at least some of the successive samples of step (b) have different volumes.

In some embodiments, the volume of the sample transferred at each step (b) is from 0.005 µL to 10 µL, preferably from 0.01 µL to 2 µL, more preferably from 0.02 to 1 µL.

In some embodiments, the absolute pressure in the first chamber at step (a) is from 100 to 1000 bar, preferably from 200 to 800 bar, more preferably from 350 to 600 bar.

In some embodiments, the temperature in the first chamber and in the second chamber is at a same predetermined value during all of steps (b) and (c).

In some embodiments, the temperature in the first chamber is equal to the temperature in the second chamber during all of steps (b) and (c).

In some embodiments, the method comprises one or more steps (c) wherein the temperature in the first chamber and/or the second chamber has a first value, followed by one or more steps (c) wherein the temperature in the first chamber and/or the second chamber has a second value different from the first value.

In some embodiments, the ratio of the fixed volume of the first chamber to the fixed volume of the second chamber is from 0.2 to 5, preferably from 0.5 to 2, and more preferably is from 0.8 to 1.25.

In some embodiments:
- the volume of the first chamber is from 5 µL to 2 mL, preferably from 10 µL to 1 mL, more preferably from 50 µL to 200 µL; and/or
- the volume of the second chamber is from 5 µL to 2 mL, preferably from 10 µL to 1 mL, more preferably from 50 µL to 200 µL In some embodiments, the method further comprises at least one step of:
- (e) transferring a portion of the hydrocarbon fluid contained in the first chamber or in the second chamber to a third chamber and measuring a pressure in the third chamber.

In some embodiments, the volume of the third chamber is at least 10 times, preferably at least 20 times, more preferably at least 100 times larger than the volume of the first chamber and than the volume of the second chamber.

In some embodiments, the method comprises, after at least some of steps (b), the additional step of:
- (c') determining the proportion of the volume of at least one of the first chamber and the second chamber which is occupied by gaseous hydrocarbon fluid or by liquid hydrocarbon fluid.

In some embodiments, the property of the hydrocarbon fluid is selected from a compressibility, a gas/oil volume ratio, a vapor pressure and a thermal expansion coefficient.

In some embodiments, the method comprises a step of calculating at least one value of the property of the hydrocarbon fluid, said calculation being based on:
- at least some of the pressure measurements of steps (c);
- optionally, the pressure measurement in the third chamber, if it is performed;
- optionally, the determination of the proportion of the volume of the first chamber and/or second chamber which is occupied by gaseous hydrocarbon fluid or by liquid hydrocarbon fluid, if it is performed;
- optionally, one or more temperature measurements in the first chamber and/or the second chamber.

The invention also relates to an apparatus for determining at least one property of a hydrocarbon fluid, comprising:
- a first chamber having a fixed volume and provided with a pressure sensor;
- a feeding system for introducing a hydrocarbon fluid into the first chamber;
- a second chamber having a fixed volume and provided with a pressure sensor;
- a transfer system configured for successively transferring samples of hydrocarbon fluid from the first chamber to the second chamber.

In some embodiments, the transfer system is configured for successively transferring samples of hydrocarbon fluid having all the same volume.

In some embodiments, the transfer system is configured for successively transferring samples of hydrocarbon fluid having different volumes.

In some embodiments, the transfer system comprises a rotative valve which comprises a rotative body having one or more cavities, said cavities being configured for alternatively being:
- in fluid communication with the first chamber,
- in fluid communication with the second chamber, and
- neither in fluid communication with the first chamber nor in fluid communication with the second chamber, depending on an angular position of the rotative body.

In some embodiments, the ratio of the volume of the first chamber to the volume of the second chamber is from 0.2 to 5, preferably from 0.5 to 2, and more preferably is from 0.8 to 1.25.

In some embodiments:
- the volume of the first chamber is from 5 µL to 2 mL, preferably from 10 µL to 1 mL, more preferably from 50 µL to 200 µL; and/or
- the volume of the second chamber is from 5 µL to 2 mL, preferably from 10 µL to 1 mL, more preferably from 50 µL to 200 µL.

In some embodiments, the feeding system is configured for introducing the hydrocarbon fluid into the first chamber at an absolute pressure of from 100 to 1000 bar, preferably from 200 to 800 bar, more preferably from 350 to 600 bar.

In some embodiments, the apparatus comprises at least one temperature sensor, preferably in the first chamber and/or in the second chamber.

In some embodiments, the apparatus comprises a temperature regulation system configured for regulating the temperature in the first chamber and/or in the second chamber, said temperature regulation system being preferably selected from a resistive heating system, a refrigerant circuit and combinations thereof.

In some embodiments, the apparatus further comprises:
- a third chamber, provided with a pressure sensor;
- a venting system configured for transferring a portion of hydrocarbon fluid from the first chamber and/or the second chamber to the third chamber.

In some embodiments, the volume of the third chamber is at least 10 times, preferably at least 20 times, more preferably at least 100 times larger than the volume of the first chamber and than the volume of the second chamber.

In some embodiments, the apparatus comprises a monitoring system for determining the proportion of the volume of at least one of the first chamber and the second chamber which is occupied by gaseous hydrocarbon fluid or by liquid hydrocarbon fluid, said monitoring system preferably comprising a camera.

In some embodiments, the apparatus comprises an analysis module configured to receive data, as an input, from:
- the pressure sensor of the first chamber and/or the pressure sensor of the second chamber;
- optionally, the at least one temperature sensor, if present;
- optionally, the pressure sensor of the third chamber, if present;
- optionally, the monitoring system, if present;

said analysis module being configured to perform a calculation based on said input data and provide analysis data as an output.

In some embodiments, the analysis data pertain to a property of the hydrocarbon fluid selected from a compressibility, a gas/oil volume ratio, a vapor pressure and a thermal expansion coefficient.

In some embodiments, the apparatus comprises a control module which is configured to send instructions for actuating the transfer system.

The invention also relates to a computer program comprising instructions for implementing the above method in the above apparatus, when the program is executed on a computer.

The invention also relates to a computer-readable storage medium on which this computer program is stored.

The invention also relates to a system comprising a processor coupled to a memory on which this computer program is stored.

The present invention addresses the need expressed in the prior art. In particular the invention provides an improved method of measuring properties of a complex hydrocarbon fluid, which is easier to implement and relies on equipment having a smaller size.

This is made possible owing to an apparatus as claimed, wherein successive samples of hydrocarbon fluid are passed from a first chamber having a fixed volume to a second chamber also having a fixed volume, and appropriate pressure measurements are performed.

DESCRIPTION OF EMBODIMENTS

Figure 1:
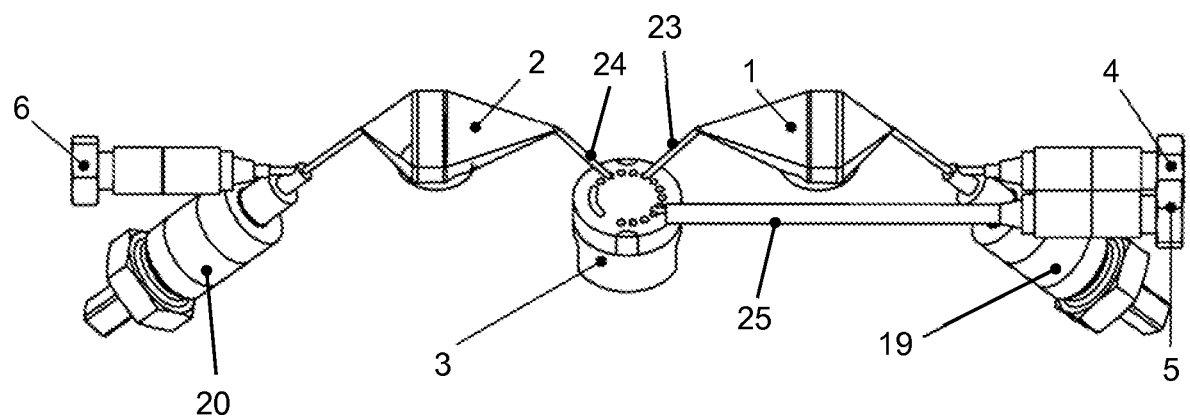
FIG. 1 schematically shows some of the main elements of the apparatus of the invention, isolated from the rest of the apparatus, according to one embodiment.

The invention will now be described in more detail without limitation in the following description.

Apparatus

Making reference mainly to FIGS. 1, 3, 4 and 5, the apparatus of the invention comprises a first chamber 1, a second chamber 2, a transfer system 3 and a feeding system 4.

The transfer system 3 is configured for successively transferring samples of fluid from the first chamber 1 to the second chamber 2, as will described in greater detail below.

The feeding system 4 is configured for introducing fluid into the first chamber 1.

The apparatus of the invention can be designed so as to accommodate elevated pressure within the first chamber 1, the second chamber 2 and the transfer system 3. The apparatus is thus preferably constructed so that it can accommodate an absolute pressure of at least 50 bar, more preferably of at least 100 bar, even more preferably of at least 200 bar, and most preferably of at least 500 bar, in at least the first chamber 1 and the transfer system 3, and desirably also in the second chamber 2.

One way to achieve the desired resistance to pressure is to provide a main block 11, which can be made of stainless steel or any other pressure-resistant material, wherein channels are e.g. carved and/or drilled so as to form the first chamber 1, the second chamber 2, as well as conduits leading to and from each of the first chamber 1 and the second chamber 2. The channels forming the first chamber 1 and second chamber 2 in the main block 11 may have open surfaces which are closed by one or, as illustrated, by two respective side blocks 12, 13 which are firmly fixed to and pressed against the main block 11 over the respective chambers 1, 2.

Optionally, respective windows 14, 15 may be provided in these side blocks 12, 13 so that the contents of the chambers 1, 2 may be monitored from the outside, owing to a monitoring system. For instance, these windows 14, 15 may be made of sapphire, or any other transparent or translucid material able to withstand high pressure. The monitoring system may comprise respective cameras so as to e.g. optically analyze the contents of the chambers 1, 2.

One or both of the first chamber 1 and second chamber 2 are preferably provided with respective pressure sensors 7, 8. To this end, the main block may be provided with cutouts communicating with the chambers 1, 2, opposite the side blocks 12, 13. The pressure sensors 7, 8 may be inserted into these cutouts. In other terms, one open surface area of each chamber 1, 2 may be closed by a respective pressure sensor 7, 8, opposite the respective side block 12, 13. The part of each pressure sensor 7, 8 in contact with the inside of the respective chamber 1, 2 can be in particular a deformable membrane the position of which depends on the pressure within the respective chamber 1, 2.

The feeding system 4 may comprise a conduit leading to the first chamber 1, as well as a connector for connecting the feeding system 4 to a source of fluid, such as a source of hydrocarbon fluid. The conduit can be e.g. drilled within the main block 11, and it can be in fluid communication with the connector.

Optionally and preferably, a venting system 6 is provided for transferring fluid contained in the second chamber 2 to a third chamber, not shown on the drawings. The venting system 6 may comprise a conduit leading to the second chamber 2 as well as a connector for connecting the venting system 6 to directly to the third chamber, or to an external conduit in fluid communication with the third chamber. The conduit of the venting system leading to the second chamber 2 can be e.g. drilled within the main block 11, and it can be in fluid communication with the connector.

It is advantageous to provide the third chamber at a distance from the main block 11 as this third chamber is preferably of a significantly larger volume than the first chamber 1 and the second chamber 2. However, the third chamber could also be provided within the main block 11 similarly to the first chamber 1 and the second chamber 2.

According to other, non-illustrated variants:
the third chamber can be connected to the first chamber 1 instead of the second chamber 2, in which case the conduit of the venting system 6 leads to the first chamber 1 instead of the second chamber 2;

each of the first chamber 1 and second chamber 2 can be connected to respective third chambers, via respective venting systems;

each of the first chamber 1 and second chamber 2 can be connected to one and the same third chamber, via respective venting systems;

the venting system 6 may be connected to the transfer system 3, so that fluid from either the first chamber 1 or the second chamber 2 may be transferred to one and the same third chamber via one and the same venting system 6.

In the illustrated embodiment, fluid ingress and egress to and from the first chamber 1 can be performed via two respective conduits, one which is part of the feeding system 4 and the other one (hereafter referred to as "the first conduit 23") which leads to the transfer system 3. A closing mechanism can be provided to close the feeding system 4 and thereby isolate the first chamber 1 from the external source of fluid. In the illustrated embodiment, said closing mechanism is a needle valve 19.

In the illustrated embodiment, fluid ingress and egress to and from the second chamber 2 can be performed via two respective conduits, one which is part of the venting system 6 and the other one (hereafter referred to as "the second conduit 23") which leads to the transfer system 3. A closing mechanism can be provided to close the venting system 6 and thereby isolate the second chamber 2 from the third chamber. In the illustrated embodiment, said closing mechanism is a needle valve 20.

Optionally and preferably, a purge system 5 is provided for purging at least one of the first chamber 1 and second chamber 2. In the illustrated embodiments, the purge system comprises a third conduit 25 connected to the transfer system 3, which can be e.g. drilled within the main block 11, as well as a connector for connecting the purge system 5 to a purging device configured to provide a vacuum within the first chamber 1 and/or the second chamber 2.

According to other, non-illustrated variants:
the purge system 5 can be connected directly to the first chamber 1 and/or to the second chamber 2 via additional conduits; or two respective purge systems can be directly and respectively connected to the first chamber 1 and the second chamber 2 via additional conduits.

The transfer system 3 is at least configured for successively transferring samples of fluid from the first chamber 1 to the second chamber 2. It may also be configured for placing the first chamber 1 and/or the second chamber 2 in fluid communication with the purge system 5, as illustrated in the drawings and as described in more detail below. In case the venting system 6 is connected to the transfer system 3 (embodiment not shown), the transfer system 3 is then also configured for placing the first chamber 1 and/or the second chamber 2 in fluid communication with said venting system 6 leading to the third chamber.

Figure 2:
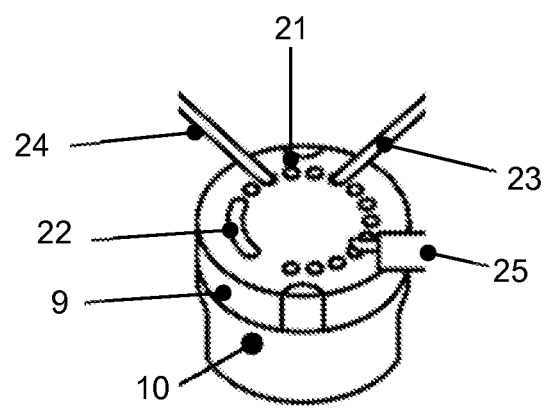
FIG. 2 is a detail taken from FIG. 1, schematically showing part of the transfer system of the apparatus, according to one embodiment.

Making reference more particularly to FIGS. 1 and 2, the transfer system 3 preferably comprises a rotative valve. Said rotative valve comprises a rotative body 9, which may preferably be disk-shaped and may preferably comprise one or more cavities 21, 22 on one of the main disk surfaces. These cavities 21, 22 can be formed as recesses in the rotative body 9. Preferably, the different cavities 21, 22 can be arranged along a circle or an arc on surface of the rotative body 9.

The rotative body 9 can be firmly pressed against the main block 11 (the cavities 21, 22 being on the surface in contact with the main block 11). The rotative body 9 is preferably made of an elastomeric material such as polyimide (for instance of the brand Vespel®). Thus, the rotative body 9 can rotate against the main block 11 in a leak-tight manner.

In the illustrated embodiment, three conduits are arranged at different fixed angular positions relative to the rotative body 9, namely the first conduit 23 in fluid communication with the first chamber 1, the second conduit 24 in fluid communication with the second chamber 2, and the third conduit 25 of the purge system 5. Additional conduits can be arranged at further angular positions if necessary, in accordance with some of the non-illustrated variants mentioned above.

When the rotative body 9 is rotated, the angular position of the cavities 21, 22 may vary. Thus, some of the cavities 21, 22 may be placed in fluid communication with one or more of the conduits 23, 24, 25 depending on the rotation of the rotative body 9.

For example, the rotative body 9 may comprise one or more small cavities 21. Depending on the rotation of the rotative body 9, one small cavity 21 may first be placed in contact with the first conduit 23, at a first angular position, so as to be in fluid communication with the first chamber 1; and then placed in contact with the second conduit 24, at a second angular position, so as to be in fluid communication with the second chamber 2. This makes it possible to transfer a sample of fluid from the first chamber 1 to the small cavity 21, and then from the small cavity 21 to the second chamber 2. The transfer of the fluid can be driven by a pressure difference between the first chamber 1 on the one hand, and the small cavity 21 and the second chamber 2 on the other hand.

When several small cavities 21 are present, they can have the same volume or different volumes.

Furthermore, the rotative body 9 can also comprise at least one larger cavity 22, which can be e.g. crescent-shaped. Depending on the rotation of the rotative body 9, this larger cavity may for instance:
- be placed in contact with both the first conduit 23 and the third conduit 25 at the same time, so as to make the first chamber 1 in fluid communication with the purge system 5 and therefore purge the first chamber 1; and/or
- be placed in contact with both the second conduit 24 and the third conduit 25 at the same time, so as to make the second chamber 2 in fluid communication with the purge system 5 and therefore purge the second chamber 2; and/or
- be placed in contact with both the first conduit 23 and the second conduit 24 at the same time, so as to make the first chamber 1 in fluid communication with the second chamber 2; and/or
- be placed in contact with the first conduit 23, the second conduit 24 and the third conduit 25 at the same time, so as to make both the first chamber 1 and the second chamber 2 in fluid communication with the purge system 5 and therefore purge both the first chamber 1 and the second chamber 2 at the same time.

Figure 3:
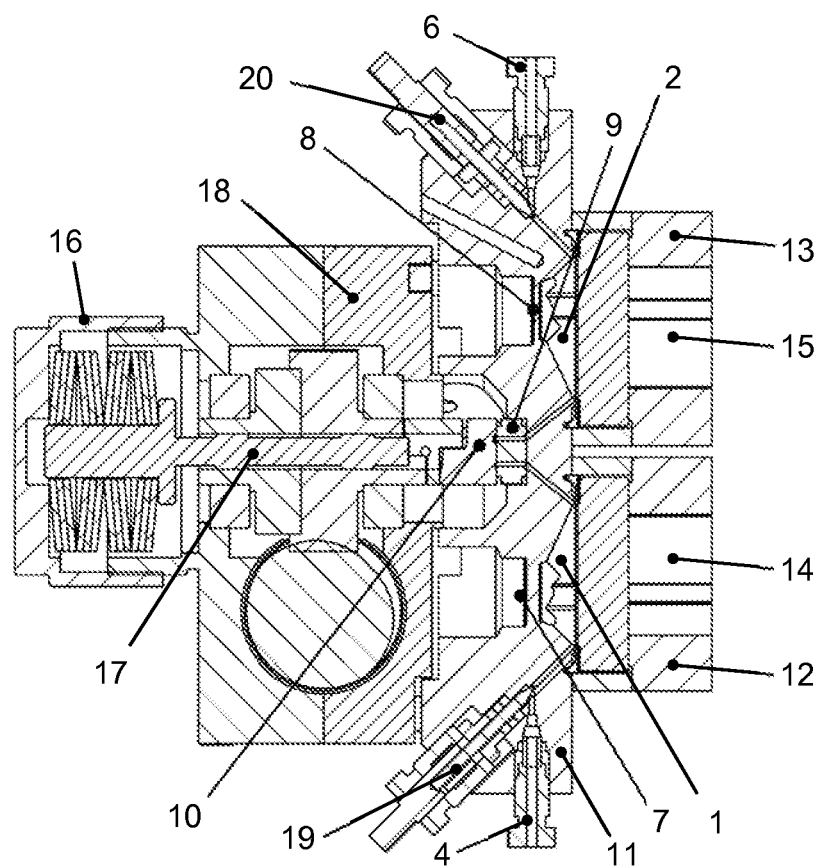
FIG. 3 is a cross-sectional view of the apparatus of the invention, according to one embodiment.
Figure 4:
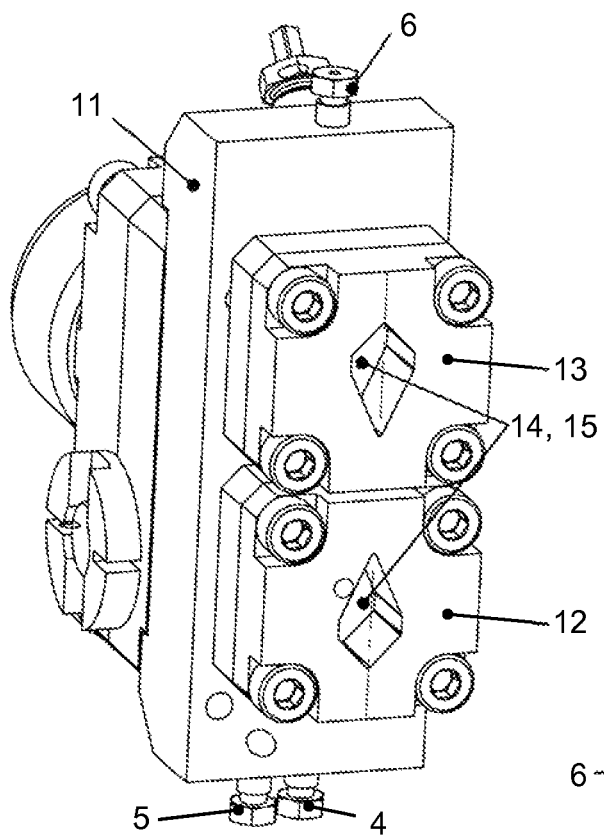
FIGS. 4 and 5 are two perspective views of the apparatus of the invention, according to one embodiment.
Figure 5:
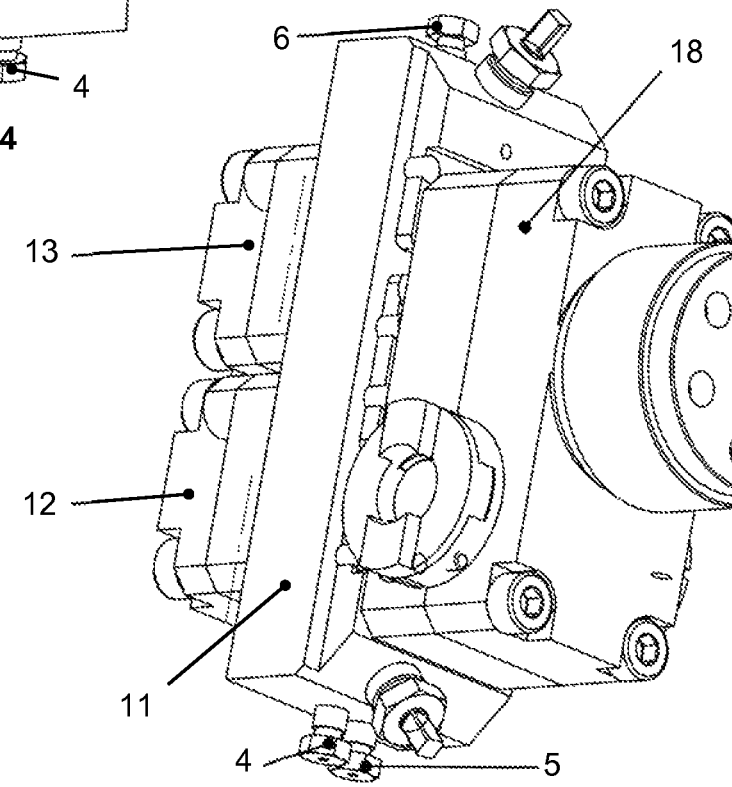

Making reference mainly to FIG. 3, rotation of the rotative body 9 can be effected owing to a shaft 17 driven by an engine 16. A speed reducing mechanism 18 is advantageously connected to the shaft 17, so as to provide a fine control of the angular position of the rotative body 9. The reducing factor can be for instance from 10 to 10,000, preferably from 100 to 5,000, more preferably from 500 to 2,000. A reducing factor of 1,000, for instance, means that 1,000 rotations of the engine-driven shaft 17 correspond to only one full rotation of the rotative body 9.

The reducing mechanism 18 can for instance drive an intermediate part 10 which bears against the rotative body 9, so as to firmly compress said rotative body 9 against the main block 11. The intermediate part 10 may for instance be made of ceramics or stainless steel. It may be disk-shaped.

In the apparatus described above, the first chamber 1 and the second chamber 2 are of a fixed, i.e. constant volume. In particular, these chambers 1, 2 are not provided with a piston or any other volume variation device. It will be appreciated that the presence of a pressure sensor in each chamber may result in infinitesimal variations in volume, as the pressure sensor typically comprises a deformable membrane. However, such infinitesimal variations in volume have no significant impact on the method described below and can thus be neglected.

The volume of the first chamber 1 and of the second chamber 2 may be different. The ratio of the volume of the first chamber 1 to the volume of the second chamber 2 may thus range from 0.2 to 5, preferably from 0.5 to 2, and more preferably is from 0.8 to 1.25. More preferably, the volume of the first chamber 1 is substantially identical to the volume of the second chamber 2 (ratio of 1). The volume of each of the first chamber 1 and second chamber 2 may for instance range from 10 µL to 10 mL, preferably from 20 µL to 1 mL, more preferably from 30 µL to 500 µL, even more preferably from 50 µL to 200 µL. Satisfactory results have been obtained with an apparatus as depicted in FIGS. 1 to 5 and having chamber volumes of 100 µL.

It may be advantageous for the first chamber 1 or the second chamber 2 (and preferably both) to have a relatively flat shape defined in a main plane. The first chamber 1 or the second chamber 2 (and preferably both) may have a main axis from an inlet to an outlet of the chamber. It may be advantageous for the cross-section of the first chamber 1 or the second chamber 2 (and preferably both) which is orthogonal to the main axis to progressively increase and then progressively decrease from the inlet to the outlet, so that the first chamber 1 or the second chamber 2 (and preferably both) may assume a general diamond or lozenge shape in the main plane. This can be in particular useful to accurately monitor the position of a gas-liquid interface in the respective chamber if necessary.

The volume of each cavity 21, 22 in the rotative body 9 may range from e.g. 0.005 µL to 10 µL, preferably from 0.01 µL to 2 µL, more preferably from 0.02 to 1 µL.

The volume of the third chamber, when present, may range from e.g. 1 mL to 10 L, preferably from 10 mL to 1 L, and more preferably from 50 mL to 200 mL.

The apparatus is preferably provided with one or more temperature sensors (such as thermocouples) and is also preferably provided with a temperature regulation system, which may comprise a heating and/or cooling system. For instance, use may be made of a refrigerant circuit and/or resistive heating.

Optionally, more than one set of first chamber 1, second chamber 2, transfer system 3 and associated conduits, connectors and piping may be provided in the apparatus. This can be useful if several measurements are to be performed in parallel so as to achieve a more accurate determination of the properties of the fluid based on a statistical analysis.

The apparatus of the invention may also comprise—or be associated in a larger system with—an analysis module and/or a control module.

The analysis module may receive data from the various pressure and/or temperature sensors, from the monitoring system, from the user and/or from the control module and provide analysis data as an output.

The control module may receive data from the user and/or from the analysis module and may send instructions which make it possible to actuate the transfer system 3 (in the illustrated embodiment, via the engine 16) as well as the various valves of the apparatus. It is possible to operate the apparatus in an automated or semi-automated manner, using appropriate computer hardware and software.

Overall, the maximum dimension of the apparatus may be less than 1 m, preferably less than 60 cm, more preferably less than 40 cm.

Overall, the volume occupied by the apparatus may be less than 100 L, preferably less than 50 L, more preferably less than 30 L, and most preferably less than 15 L.

Therefore, the apparatus may be portable. It may also be placed in an extraction well if desired.

Method

The invention provides a method for determining at least one property of a fluid. More specifically, the method is applied to a hydrocarbon fluid as described below. However, it will be understood that the method may similarly be applied to other types of fluids, in particular complex fluids comprising a mixture of different chemical compounds.

The hydrocarbon fluid used in the method of the invention is preferably a hydrocarbon fluid recovered from a subterranean formation. It is preferably a complex fluid comprising various hydrocarbon compounds and optionally water as well as contaminants or chemicals used in the process of hydrocarbon recovery (surfactants, carbon dioxide, etc.).

In the following, for illustrative purposes, the method is implemented in the apparatus described above.

As a preliminary step in the method, it may be desirable to purge the first chamber 1 and the second chamber 2 (and optionally the third chamber, if present) from any material present therein. To this end, the purge system 5 may be connected to the first chamber 1 and/or the second chamber 2, for example via the transfer system 3 as illustrated, and a vacuum may be applied so as to substantially empty the first chamber 1 and/or the second chamber 2. The first chamber 1 and/or the second chamber 2 may thus be depressurized down to an absolute pressure of less than 0.1 bar, or less than 0.01 bar, or less than 0.002 bar or less than 0.001 bar.

After this preliminary purging step, the first chamber 1 is fluidically isolated from the second chamber 2 by a proper setting of the transfer system 3. In the illustrated embodiment, the second chamber 2 is also fluidically isolated from the third chamber (not shown) by closing the venting system 6 (e.g. owing to the needle valve 20).

Then the first chamber 1 is filled with hydrocarbon fluid owing to the feeding system 4.

The hydrocarbon fluid is introduced into the first chamber 1 under elevated pressure, i.e. preferably at an absolute pressure of at least 50 bar, or at least 100 bar, or at least 200 bar, or at least 300 bar, or at least 400 bar, or at least 500 bar. In particular, possible absolute pressure ranges at this step are from 100 to 1000 bar, preferably from 200 to 800 bar, more preferably from 350 to 600 bar.

At this step, the hydrocarbon fluid in the first chamber 1 is preferably in a liquid and/or supercritical state. It preferably does not comprise any gaseous fraction.

The pressure of the hydrocarbon fluid in the first chamber 1 at the introduction stage can be achieved directly owing to the pressure of the source of hydrocarbon fluid, notably if the apparatus is placed within an extraction well so as to collect hydrocarbon fluid from the subterranean formation in situ. Alternatively, a pump may be used to pressurize the hydrocarbon fluid directed to the apparatus.

After the introduction step, the method of the invention comprises a succession of respective steps of:
  transferring a sample of hydrocarbon fluid from the first chamber 1 to the second chamber 2, via the transfer system 3; and
  measuring a pressure in at least one of the first chamber 1 and the second chamber 2 (and preferably both in the first chamber 1 and the second chamber 2).

These two steps can be repeated a plurality of times, for instance from 5 to 1,000 times, preferably from 10 to 500 times, more preferably from 20 to 200 times.

The pressure in the second chamber 2 is initially low, as the second chamber 2 is initially substantially empty. Typically, the pressure in the second chamber 2 at this stage can be 1 bar or less than 1 bar if the second chamber 2 has been purged as described above. On the other hand, the pressure of the first chamber 1 is initially high, as described above. Successive samples of hydrocarbon fluid are thus transferred from the first chamber 1 to the second chamber 2 owing to this difference in pressure, by properly actuating the transfer system 3. Therefore, the pressure in the first chamber 1 tends to decrease over time while the pressure in the second chamber 2 tends to increase over time.

Figure 6:
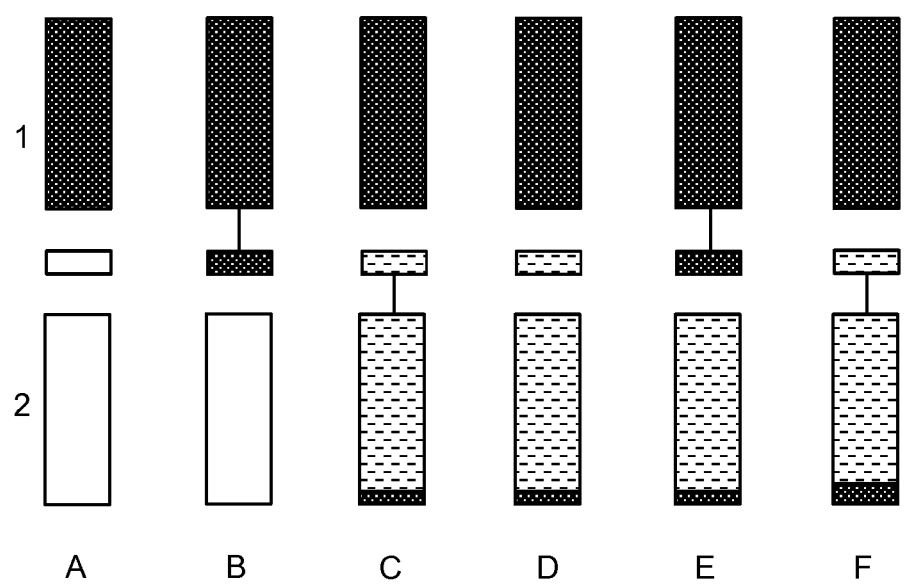
FIG. 6 is a diagram schematically showing how the hydrocarbon fluid is handled in successive steps of the method of the invention.

The schematic depiction in FIG. 6 shows some of the first stages of the method:
  A: the first chamber 1 is filled with hydrocarbon fluid, while the second chamber 2 is substantially empty;
  B: a sample of fluid is collected from the first chamber 1, via the transfer system 3 (in the embodiment illustrated above, a cavity 21 of the rotative body 9 is in fluid communication with the first chamber 1);
  C: this sample of fluid is passed to the second chamber 2, via the transfer system 3 (in the embodiment illustrated above, the above cavity 21 of the rotative body 9 is in fluid communication with the second chamber 2) and a pressure measurement is performed;
  D: in an optional intermediate stage both chambers may be isolated from the transfer system 3 (i.e. no cavity 21 of the rotative body 9 is in fluid communication with either chamber 1, 2);
  E: as a repetition of stage B, another sample of fluid is collected from the first chamber 1, via the transfer system 3;
  F: as a repetition of stage C, said other sample of fluid is passed to the second chamber 2, via the transfer system 3 and a pressure measurement is performed.

It should be noted that some of these stages may be performed concomitantly, e.g. by using different cavities 21 of the rotative body 9. For instance, stage C can be performed simultaneously with stage D and/or E, if a different cavity 21 is used at stage C than at stage D and/or E.

Preferably, during at least a first series of transferring steps, the pressure in the second chamber 2 is lower than the pressure in the first chamber 1, such that:
  the hydrocarbon fluid in the first chamber 1 generally remains in a liquid or supercritical state; and
  the hydrocarbon fluid in the second chamber 1 is generally in the gaseous state or comprises at least two phases, including a gaseous phase and a liquid phase; if necessary, the respective volume proportions of the gaseous phase and the liquid phase may be determined by monitoring the interface between these respective phases in the chamber.

Preferably, during at least a second series of transferring steps (namely after the vapor pressure has been reached in the first chamber 1), the hydrocarbon fluid in the first chamber 1 comprises at least two phases, including a gaseous phase and a liquid phase.

During this second series of transferring steps, either samples of the liquid phase or samples of the gaseous phase in the first chamber 1 may be transferred to the second chamber 2.

In the example illustrated in FIG. 6, it is assumed that the conduit connecting the first chamber 1 to the transfer system 3 is connected at the bottom of the first chamber 1 (the first chamber 1 being above the second chamber 2, and the transfer system 3 being between the two chambers 1, 2). In this case, samples of the liquid phase are transferred from the first chamber 1 to the second chamber 2.

However, it is also possible that the conduit connecting the first chamber 1 to the transfer system 3 may be connected at the top of the first chamber 1 (the first chamber 1 being below the second chamber 2, and the transfer system 3 being between the two chambers 1, 2). In this case, samples of the gaseous phase are transferred from the first chamber 1 to the second chamber 2.

Switching from one configuration to the other may be easily performed simply by turning the apparatus upside down.

The transfers of samples may be stopped once the pressure in the first chamber 1 is equal to the pressure in the second chamber 2, or they can be stopped before reaching that point.

As already mentioned above, in the successive steps of transferring a sample of hydrocarbon fluid from the first chamber 1 to the second chamber 2, all samples may have the same unitary volume, or samples of different volumes may be used. Using samples having a larger volume may be advantageous if the measured pressure tends to vary little at each step, whereas using samples having a smaller volume may be advantageous if the measured pressure tends to vary a lot at each step.

The volume of the sample transferred at each step may for example range from 0.005 to 10 μL, preferably from 0.01 to 2 μL, more preferably from 0.02 to 1 μL.

The temperature in the chambers 1, 2 may remain constant over time. Alternatively, the temperature in the chambers 1, 2 may be varied over time.

In some embodiments, the temperature in each chamber 1, 2 can be independently controlled. In an alternative, simpler embodiment, the temperature of both chambers 1, 2 is controlled similarly.

Various properties of the hydrocarbon fluid may be determined owing to the method of the invention.

By way of example, the vapor pressure of the hydrocarbon fluid at a given temperature may be determined as follows. The pressure in the first chamber 1 is plotted as a function of the cumulative volume of fluid transferred from the first chamber 1 to the second chamber 2. The vapor pressure is reached when the first bubble of gas appears in the first chamber 1. This corresponds to a sudden change in the slope of the plotted pressure.

By way of example, the isothermal compressibility of the hydrocarbon fluid at a given temperature, in a monophasic state, may be determined as follows. The pressure in the first chamber 1 is plotted as a function of the cumulative volume of fluid transferred from the first chamber 1 to the second chamber 2, before the first bubble of gas appears in the first chamber 1. The compressibility of the fluid is calculated based on the slope of the plotted pressure. More specifically, it is inversely proportional to this slope.

By way of example, the gas/oil volume ratio of the hydrocarbon fluid at a given temperature, in a biphasic state, may be determined as follows. The pressure in the second chamber 2 is plotted as a function of the cumulative volume of fluid transferred from the first chamber 1 to the second chamber 2. The gas/oil volume ratio may be calculated based on the slope of the plotted pressure.

By way of example, the thermal expansion coefficient of the hydrocarbon fluid, in a monophasic state, at a given pressure, may be determined as follows. At one particular step of the process, the pressure in one of the first chamber 1 or second chamber 2 is measured. Then the temperature is varied, and the pressure is measured again. Based on the result of this measurement, and based on the isothermal compressibility which can be calculated as explained above, the thermal expansion coefficient of the fluid in the relevant chamber can be calculated.

Other determinations may be performed, also based on the proportion of the volume of the first chamber 1 and/or of the second chamber 2 occupied by a liquid and/or occupied by a gas.

After performing a number of steps of transferring samples from one chamber to the other and measuring the pressure in the chambers, it is possible to transfer a portion of the fluid contained in the first chamber 1 or in the second chamber 2 to the third chamber, which preferably has a volume much larger than the volume of the first chamber 1 and second chamber 2. The transfer may be effected by simply placing the first chamber 1 or the second chamber 2 in fluid communication with the third chamber which is at a lower pressure than the first chamber 1/second chamber 2 (such as an absolute pressure of 1 bar, or less than 1 bar if a vacuum has previously been applied to this third chamber).

Preferably, the portion of the fluid transferred to the third chamber corresponds to substantially all the gaseous phase in the first chamber 1 or second chamber 2 (due to the large difference in volume between the first chamber 1 or second chamber 2 and the third chamber). In other terms, this represents a step of gas expansion.

A pressure measurement after this step of gas expansion makes it possible to calculate for instance the compressibility factor of the gas, i.e. to determine how the gas deviates from a perfect gas.

The invention claimed is:

1. A method for determining at least one property of a hydrocarbon fluid, comprising:
   (a) providing a first chamber filled with the hydrocarbon fluid and a second chamber which is substantially empty, each of the first chamber and second chamber having a fixed volume;
   (b) transferring a sample of hydrocarbon fluid from the first chamber to the second chamber;
   (c) measuring a pressure in at least one of the first chamber and the second chamber; and
   (d) repeating steps (b) and (c) a plurality of times, wherein the pressure in the first chamber decreases over time as successive samples are transferred from the first chamber to the second chamber.

2. The method of claim 1, wherein step (c) comprises measuring a pressure both in the first chamber and in the second chamber.

3. The method of claim 1, wherein the volume of the sample transferred at each step (b) is from 0.005 μL to 10 μL.

4. The method of claim 1, wherein the temperature in the first chamber and in the second chamber is at a same predetermined value during all of steps (b) and (c); or wherein the temperature in the first chamber is equal to the temperature in the second chamber during all of steps (b) and (c).

5. The method of claim 1, wherein the ratio of the fixed volume of the first chamber to the fixed volume of the second chamber is from 0.2 to 5.

6. The method of claim 1, wherein:
the volume of the first chamber is from 5 µL to 2 mL; and/or
the volume of the second chamber is from 5 µL to 2 mL.

7. The method of claim 1, which further comprises at least one step of:
(e) transferring a portion of the hydrocarbon fluid contained in the first chamber or in the second chamber to a third chamber and measuring a pressure in the third chamber.

8. The method of claim 7, wherein the volume of the third chamber is at least 10 times larger than the volume of the first chamber and than the volume of the second chamber.

9. The method of claim 1, comprising after at least some of steps (b), the additional step of:
(c') determining the proportion of the volume of at least one of the first chamber and the second chamber which is occupied by gaseous hydrocarbon fluid or by liquid hydrocarbon fluid.

10. The method of claim 1, wherein the property of the hydrocarbon fluid is selected from a compressibility, a gas/oil volume ratio, a vapor pressure and a thermal expansion coefficient.

11. An apparatus for determining at least one property of a hydrocarbon fluid, comprising:
a first chamber having a fixed volume and provided with a pressure sensor;
a feeding system for introducing a hydrocarbon fluid into the first chamber;
a second chamber having a fixed volume and provided with a pressure sensor;
a transfer system configured for successively transferring samples of hydrocarbon fluid from the first chamber to the second chamber, and further configured for making the pressure in the first chamber decrease over time as the samples are successively transferred.

12. The apparatus of claim 11, wherein the transfer system is configured for successively transferring samples of hydrocarbon fluid having all the same volume or wherein the transfer system is configured for successively transferring samples of hydrocarbon fluid having different volumes.

13. The apparatus of claim 11, wherein the transfer system comprises a rotative valve which comprises a rotative body having one or more cavities, said cavities being configured for alternatively being:
in fluid communication with the first chamber,
in fluid communication with the second chamber, and
neither in fluid communication with the first chamber nor in fluid communication with the second chamber,
depending on an angular position of the rotative body.

14. The apparatus of claim 11, wherein the ratio of the volume of the first chamber to the volume of the second chamber is from 0.2 to 5.

15. The apparatus of claim 11, wherein:
the volume of the first chamber is from 5 µL to 2 mL; and/or
the volume of the second chamber is from 5 µL to 2 mL.

16. The apparatus of claim 11, comprising at least one temperature sensor; and/or comprising a temperature regulation system configured for regulating the temperature in the first chamber and/or in the second chamber; and/or comprising a monitoring system for determining the proportion of the volume of at least one of the first chamber and the second chamber which is occupied by gaseous hydrocarbon fluid or by liquid hydrocarbon fluid.

17. The apparatus of claim 11, further comprising:
a third chamber, provided with a pressure sensor;
a venting system configured for transferring a portion of hydrocarbon fluid from the first chamber and/or the second chamber to the third chamber.

18. The apparatus of claim 17, wherein the volume of the third chamber is at least 10 times larger than the volume of the first chamber- and than the volume of the second chamber.

19. The apparatus of claim 11, comprising an analysis module configured to receive data, as an input, from:
the pressure sensor of the first chamber and/or the pressure sensor of the second chamber;
optionally, the at least one temperature sensor, if present;
optionally, the pressure sensor of the third chamber, if present;
optionally, the monitoring system, if present;
said analysis module being configured to perform a calculation based on said
input data and provide analysis data as an output.

20. The apparatus of claim 19, wherein the analysis data pertain to a property of the hydrocarbon fluid selected from a compressibility, a gas/oil volume ratio, a vapor pressure and a thermal expansion coefficient.

* * * * *